United States Patent [19]
Noren et al.

[11] Patent Number: 5,649,966
[45] Date of Patent: Jul. 22, 1997

[54] METHOD AND APPARATUS FOR APPLYING ELECTRICAL SIGNALS TO A HEART FOR THERAPY OR DIAGNOSIS

[75] Inventors: Kjell Noren, Solna; Jakub Hirschberg, Täby, both of Sweden

[73] Assignee: Pacesetter AB, Solna, Sweden

[21] Appl. No.: 603,455

[22] Filed: Feb. 20, 1996

[30] Foreign Application Priority Data

Feb. 20, 1995 [SE] Sweden .................. 95006201

[51] Int. Cl.⁶ ...................................... A61N 1/368
[52] U.S. Cl. ............................................ 607/4
[58] Field of Search ............................ 607/4, 5, 6, 7, 607/8

[56] References Cited

FOREIGN PATENT DOCUMENTS 0 314 078  10/1988  European Pat. Off.

OTHER PUBLICATIONS

"Patent Abstracts of Japan," Apr. 17, 1992, Abstract for Japanese Application 4-117967.

Primary Examiner—William E. Kamm
Assistant Examiner—Scott M. Getzow
Attorney, Agent, or Firm—Hill, Steadman & Simpson

[57] ABSTRACT

In a method and apparatus for stimulating and/or diagnosing the heart, a voltage is applied to the heart over at least a selected portion of the heart during an activation interval with a rise and fall, with the voltage having a first derivative with an absolute value that is less than the value of the derivative which, for a patient in question, would trigger the patient's heartbeat, and with a duration from beginning to end of each applied voltage signal of at least 30 ms.

34 Claims, 3 Drawing Sheets

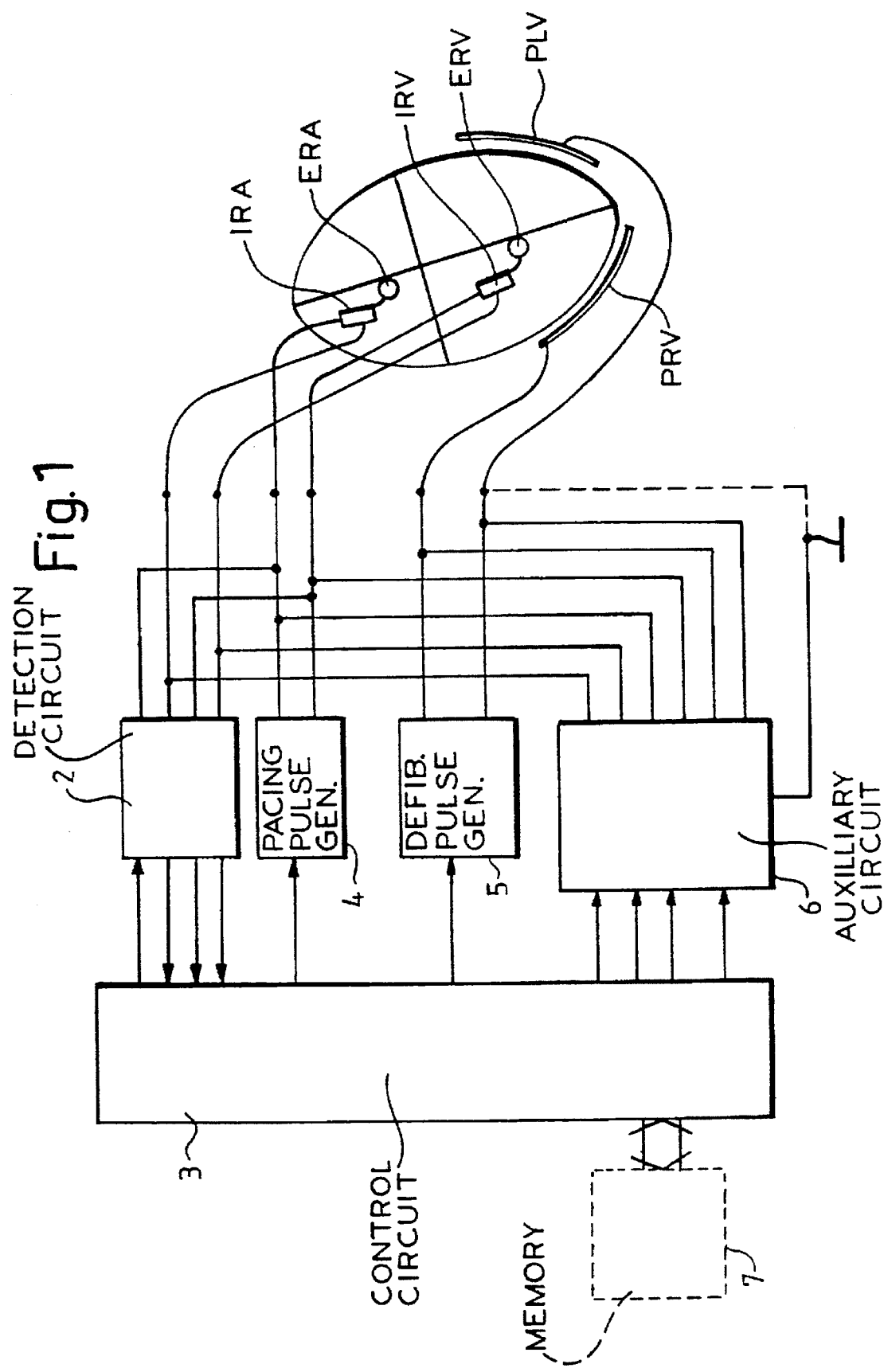

1

METHOD AND APPARATUS FOR APPLYING ELECTRICAL SIGNALS TO A HEART FOR THERAPY OR DIAGNOSIS

BACKGROUND OF THE INVENTION

1. Field of the Invention

The invention relates to a method and apparatus for heart stimulation and/or diagnosis of the type wherein the polarity and duration of voltage applied to the heart can be varied.

2. Description of the Prior Art

Devices for heart stimulation, especially as implants but also for external placement, are known in a wide range of variations. The most common is the pacemaker, which by the controlled application of electrical pulses to the heart can control the beating of the heart, either completely when the heart's natural pumping function is lost due to disease or impairment, or as a controlled supplement to intermittent natural beating. A pacemaker is often designed with the capability of also affecting a defibrillation function, i.e., for emitting powerful current shocks intended to break an unsuitable arrhythmic state (e.g. fibrillation). This is a rather forceful method of treatment and for many years there has been a desire to achieve gentler means of terminating and preventing such states.

In commonly occurring malfunctions of the heart muscles, instead of a consistent "ignition sequence" propagating in a natural manner from the sinus node to produce a satisfactory heartbeat, there is a type of cyclical process which does not dissipate after a full contraction but can continue as local contractions to no purpose. The conduction system has collapsed. A relatively mild therapy for correcting or restoring this system is desirable.

SUMMARY OF THE INVENTION

It is an object of the present invention to provide an electrical influence on the heart which in a gentle manner reduces the occurrence of malfunctions in the muscles of the heart.

Another object of the invention is to provide an electrical effect on the heart which can be employed to stop fibrillation and tachycardia at an early stage.

Another object of the invention is to provide an electrical effect on the heart which can be used together with pacing pulse stimulation and/or stimulation through defibrillation of the heart.

A further object of the invention is to provide measurements of cardiac functions under special conditions for diagnostic purposes.

By applying a direct current field over the heart, it has surprisingly been shown in tests that it is possible to achieve a recovery of the correct conduction system in the heart muscles. In general, this application of dc current should be temporary and prompted by a demonstrated need.

It is also been demonstrated that the cardiac ECG will be markedly changed so that special disease states can be diagnosed by applying a dc field.

In certain cases there can, however, be a need for long term therapeutic application of a dc field. The dc field can then be applied over the electrodes. An electrode, which in this case acts as an anode, can then cause an undesirable stimulation of the tissue with which it is in contact. In such cases it is an advantage if the dc field changes polarity periodically. Thus in such cases an alternating current with a low frequency relative to the heartbeat is applied to the heart.

In accordance with the invention it is important that the leading edge and the trailing edge of the voltage application increases or decreases so slowly that no heartbeat is triggered. The decay period (tail) should be just as long as the rise period but in the opposite direction. The rise period and the decay period need not, however, be identical. Furthermore all signal transitions should be gently rounded, also to avoid triggering a heartbeat. The absolute value of the derivative of the signal should be less, over the entire curve, than 600 volts/second. The duration of the applied voltage must be made long relative to the length of the pace pulser (about 1 ms) or of the defibrillating pulse (less than about 10 ms) and should therefore preferably exceed 30 ms, but is of course dependent on the individual in question and can therefore in certain cases be shorter. The duration can, however, extend over a number of heartbeats and in certain cases over hours and days.

Without intending to restrict the present disclosure to a particular explanation, it is assumed at present that the observed effect depends on the particular electrical/electrochemical conditions in the active heart cells. The polarization in most heart cells at rest is about −90 mV, with the inside negatively charged relative to the outside. An electric disturbance exceeding a certain threshold value causes a reversal of the cell polarity, a depolarization. The amplitude of the action potential causing this to occur is about 110 mV and the voltage differential between the cell's interior and exterior is then +20 mV. Repolarization occurs spontaneously. The process is associated with the contraction of the muscle cell.

It is assumed that application of a constant voltage field over the heart muscles with a voltage differential between two electrodes causes the absolute potential for the exterior of the cells in the potential field to be changed. A change in potential caused by the applied voltage due to the dc field may conceivably be insufficient to trigger the polarization.

In experiments on pigs, it has for example been shown that by applying an electric field (of 4 V) in the direction of the axis of the heart, a phase shift was obtained between the atrium and ventricular depolarizations sufficient so that they will occur at the same time.

In accordance with a further development of the invention, a number of electrodes are arranged relative to the heart which can provide different types of fields by suitable application of potentials.

With four electrodes in a single plane, it is possible to obtain for example a dipole field in virtually any direction within this plane.

When operating in conjunction with pacing pulses, it is suitable to ensure that the field is applied when the pulse is applied, either by synchronization or by applying the field for so a long period that synchronization is not necessary. The application of the field itself and its subsequent dismantling must occur sufficiently slowly (long rising and falling times) so that it will not cause any depolarization effect.

DESCRIPTION OF THE DRAWINGS

FIG. 1 shows a block diagram of one embodiment of a heart stimulation device constructed and operating according to the invention.

DESCRIPTION OF THE PREFERRED EMBODIMENTS

Figure 2A:
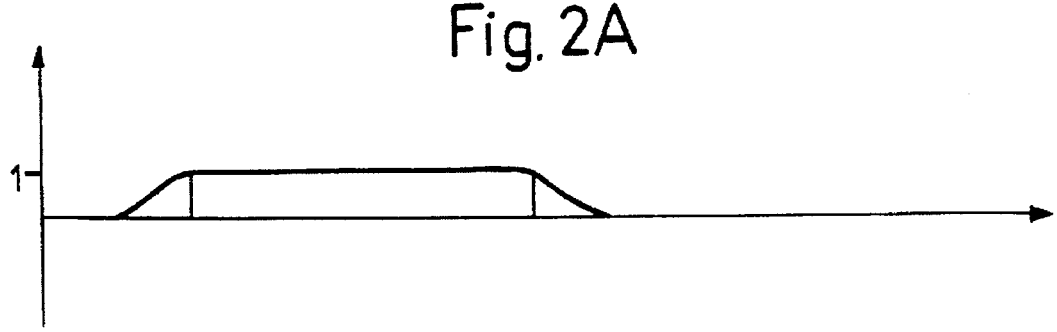
FIGS. 2A–2E respectively show various types of possible signal shapes which can be used according to the invention.

FIG. 1 schematically shows a heart 1 in which an electrode set (a tip electrode ERA and a ring electrode IRA) has been inserted in the upper right atrium and an electrode set (a tip electrode ERV and a ring electrode IRV) has been placed in the right ventricle. A first epicardial ventricle electrode PRV is placed exterior of the heart directly outside its right ventricle. A second epicardial ventricle electrode PLV is placed exterior of the heart directly outside its left ventricle.

This is a possible electrode configuration for treatment of a heart which is subject to "flutter" or "fibrillation". The electrode configuration is coupled to an implanted pacemaker/defibrillator, shown schematically at the left in FIG. 1.

Depending on the type of cardiac fault, the electrode set ERA, IRA or ERV, IRV need not be used.

The atrial functioning of the heart is measured between ERA/IRA and its ventricular function is measured between ERV/IRV. These signals are detected in a detection circuit 2 to which the electrodes are coupled. The detection circuit 2 compares the incoming signals with special predetermined conditions stored in a memory in the detection circuit 2, these conditions (when satisfied) prompting electrical cardiac stimulations of various types. When one of these conditions is fulfilled, a signal uniquely identifying that condition is fed to a control circuit 3 which selects the appropriate therapeutic steps to be taken. In FIG. 1, several outputs are shown from the detection circuit 2 to the control circuit 3 to indicate that different conditions give different types of signals.

It should be observed that a heart stimulation device implanted in a patient's body should require as little energy as possible so as to be able to function for as long as possible without battery replacement, since such replacement requires subjecting the patient to further surgery. As in conventional pacing/pacemaker treatment, the instantaneous cardiac activity of the heart is measured for example by the electrodes ERA and/or ERV. Transmission between the circuits 2 and 3 and the calculations in the circuit 3 can of course be undertaken in an analog or in a digital manner. The circuit designs themselves are known and do not constitute any portion of the invention. They are simple for a person skilled in the art to construct once informed of the desired function, and are therefore not shown here.

If the conditions for sending pacing pulses to ERA and/or ERV are fulfilled, the control circuit 3 activates a pacing pulse generating circuit 4 coupled to the electrodes ERA and ERV to provide one or more pacing pulses. These are delivered between each electrode and a reference voltage $V_{ref}$ with a displacement between them.

If the conditions for applying a defibrillation pulse or pulses are fulfilled, the control circuit 3 activates a defibrillator pulse generating circuit 5 coupled to PRV and PLV to provide some type of defibrillation pulse or defibrillation pulse sequence.

The above is known in the art and need not be described in more detail herein. The various circuits can operate and be controlled in a more or less complicated manner, as needed, which need not be described in more detail. It should be observed, however, that the various types and combinations of pacing pulses, pacing pulse sequences, defibrillation pulses and defibrillation pulse sequences can be utilized simultaneously with the therapy provided by the invention.

It should also be observed that any of the above-mentioned circuits can be eliminated, for example circuit 4 and/or circuit 5, without departing from the scope of the invention.

According to the invention, an auxiliary circuit 6 is provided that is controlled by the control circuit 3. The auxiliary circuit 6 is shown in FIG. 1 coupled to all of the electrodes outside and within the heart. This is due to the fact that for different states of the heart and/or for different conditions regarding the detected signals, it can be suitable to apply the long or low frequency non-stimulation triggering signal according to the invention between various of the electrodes shown and/or between them and a reference potential $V_{ref}$ which is suitably on the casing of the implanted stimulating device according to the invention. It is also possible to provide a number of the electrodes, for example three of the electrodes, with simultaneous current or to provide a multi-phase treatment.

In individual cases it may only be required to apply a slowly varying stimulation signal across only two of the electrodes, for example between the ventricular electrodes PRV and PLV, or between the ring electrodes IRA and IRV. In such a case the connection to the other electrodes from the auxiliary circuit 6 are not required other electrodes can then be eliminated, unless they are required for another type of treatment.

As stated above, the voltage application according to the invention can assume various forms. It can consist of a single voltage application during a certain time period with a certain polarity, or it can consist of a slowly varying alternating current, or it can consist of a voltage application during a certain time period with one polarity followed by a period without extra voltage application and thereafter followed by a voltage application with the opposite polarity or alternatively with the same polarity, etc.

Measuring cardiac activity can be effected during voltage application externally or internally with the detection circuit 2 for diagnosis of the heart. This can be done, for example, during a medical check-up. An ECG (electrocardiogram) is a sequence of signals corresponding to various electrical cardiac events. These can be registered using electrodes on the surface of the body or with electrodes in the heart, as is shown in FIG. 1. The relevant signal portions during a heartbeat are conventionally identified with the letters P, QRS (or merely R), T, where P corresponds to atrial polarization, QRS to ventricular polarization and T to ventricular repolarization. An ECG is a diagnostically useful aid for studying, for example, damage to the heart muscle and its conduction system.

When applying low voltage direct current over portions of the heart, there is a distortion of the ECG, for example the above-mentioned phase shift between the atrial and ventricular depolarizations. This distortion will be different for different pathological cardiac conditions and for different types of voltage application. An ECG obtained during a slowly applied voltage over the heart, possibly with varying electrode configuration according to a predetermined pattern, can thus provide essential and detailed information to the examining physician concerning the state of the patient's heart. The arrangement according to the invention can therefore be used both for diagnosis and therapy.

Figure 2B:
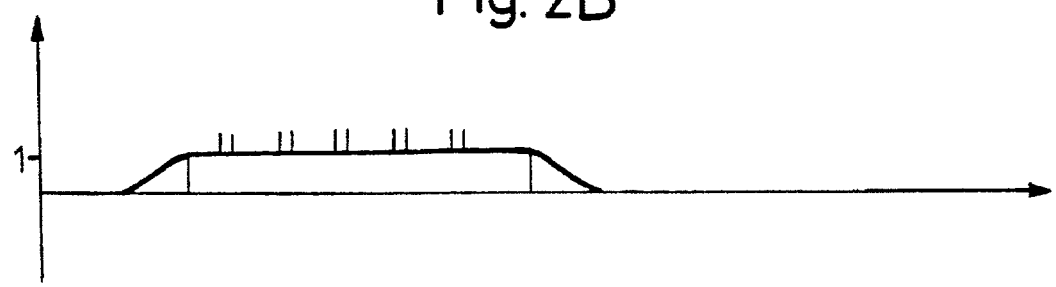
Figure 2C:
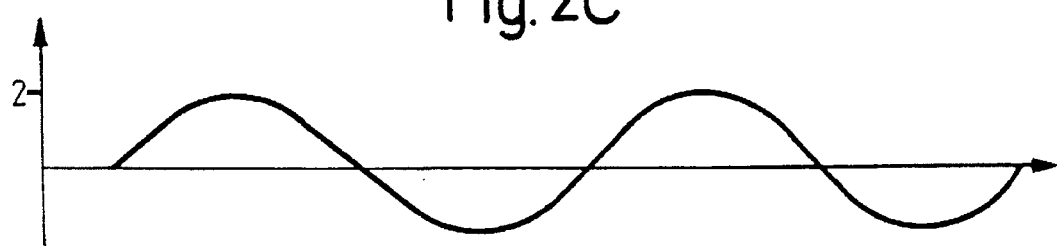
Figure 2D:
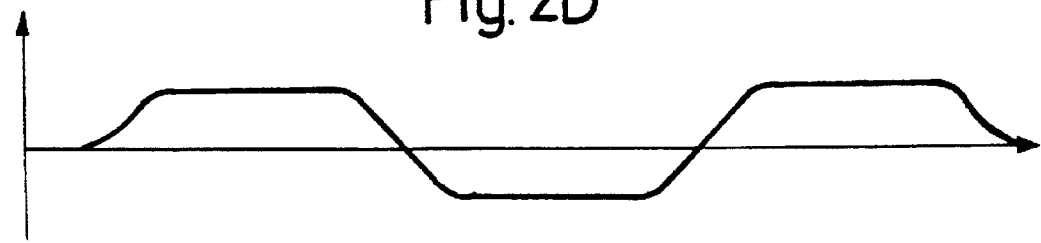
Figure 2E:
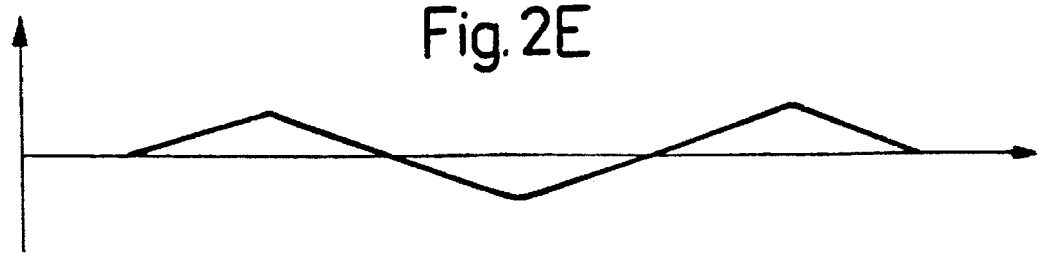

FIGS. 2A–2E respectively show various curve shapes of the voltage application according to the invention. FIG. 2A shows a voltage application during a certain number of heartbeats with a "soft" start, a period of increase of approximately 400 V/sec up to approximately 2 V with a "soft" transition to a constant voltage, followed by a gently falling curve to 0 V. FIG. 2B shows the same curve as in FIG. 2A but with superimposed pacing pulses. FIG. 2C shows an applied sinus wave with a frequency that, for example, can be 1 Hz, and with an amplitude of approximately 2 V. FIG. 2D shows a voltage application with very slowly alternating pulses with the pulse shape shown in FIGS. 2A and 2B. FIG. 2E shows that the voltage application can also have triangular shape. The pacing pulse stimulation and the defibrillation stimulation can occur at the same time with each type of curve shape for voltage application according to the invention. Today, different voltage amplitudes are used depending on the method of cardiac stimulation:

implantable perivenous and epicardial systems, 0–10 V, transcutaneous and esophageal diagnostic and ambulatory heart stimulations, 0–20 V.

It is important that the frequency of the voltage application be sufficiently low so as to not effect triggering (depolarization) of the cells. It should therefore exceed ten times the maximum conceivable pacing pulse duration, which approximately corresponds to a duration of a half-period of 30 ms, which means that the duration from beginning to the end of each applied voltage signal will probably be at least 30 ms. The absolute value of the first derivative of each portion of the applied therapy voltage should, for most patients, be less than 600 V/sec in order not to cause a triggering of the heart. The amplitude of the applied voltage should be as low as possible while still achieving the required effect (a physiologically acceptable voltage is assumed). This involves an amplitude of from about 60 mV to approximately 10 V, with a current between 0 and 10 mA. It should be observed that the limits given here can be extended if there are special needs, provided only that the voltage application is physiologically acceptable to the patient.

Probably during the application of the voltage, at least when it is positive, normal heart cells are caused to act as sinus cells, thereby producing active stimulation. The heart can for example be caused to beat more rapidly thereby. A suitable level for the individual heart is best determined by analyzing the signals received from the measuring electrode or measuring electrodes ERA, ERV.

An advantage with the therapy which can be provided with the stimulation unit according to the invention is that it can be employed at a significantly earlier stage, when the heart comes into an arrhythmic state, than the time conventionally suitable for starting defibrillation. The conditions for defibrillation are relatively strict. The stimulation according to the invention can thus be employed even in cases of moderate ventricular and atrial arrhythmias.

In order to determine the suitable voltage level for the individual, in whom the stimulation device implanted, the voltage is applied upon the onset of arrhythmia in question (with the less strict conditions for employment) and the applied voltage is increased very slowly.

Determination of when the arrhythmia declines or ceases can be done continually during a certain time period with increasing voltage. Thereafter, the voltage can be kept constant during a certain period of time and thereafter slowly decreased. The voltage amplitude at which the therapy had an effect can be stored in a memory 7 to be used upon a later occurrence of the arrhythmia. To reach the suitable voltage level, a leading edge or curve for the voltage increase can be standardized during the above described determination phase, having a steepness which is less than that of a steepness which would trigger the patient's heart.

Upon later occurrences of the arrhythmia, if the detection by the circuit 2 during treatment should show poor effect on the cardiac arrhythmia, there can be a new increase in the voltage level until a good effect is obtained and this will be stored in the memory 7. The applied voltage should, however, not be too large.

Figure 3:
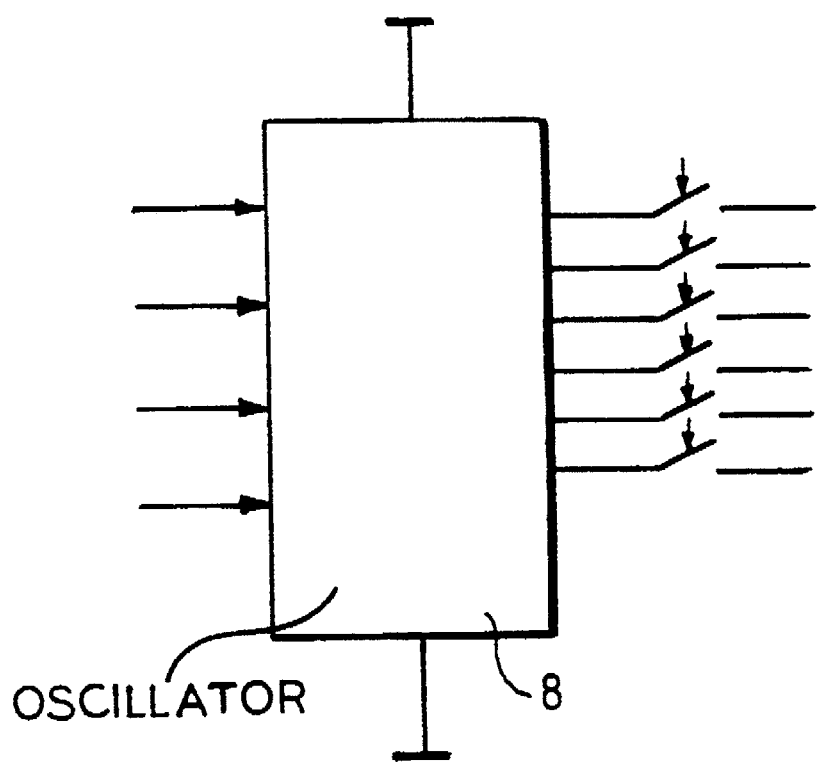
FIG. 3 shows a simple block diagram of one embodiment of a circuit for conducting therapy with voltage application according to the invention.

As shown in FIG. 3, one embodiment of the circuit 6 can include an oscillator 8, which can be controlled by the control circuit 3 with regard to frequency, amplitude and curve shape. The control circuit 3 can also turn the oscillator 8 on and 30 off. The control circuit 3 can also control the connection of the oscillator 8 to various combinations of the electrodes placed in and outside the heart. The detector circuit 2 also sends information to the control circuit concerning the timing of the heartbeat. The control circuit 3 waits until after a fully completed heartbeat with a dissipated so-called T-pulse before initiating an activation interval according to the invention.

A special effect can be achieved by controlling, in a cyclical sequence, during a first interval the voltage application between the ventricular electrodes PRV and PLV, during a second interval the voltage application between the tip electrodes ERA and ERV, and during a third interval the voltage application between the ring electrodes IRA and IRV and, for example, conducting this control at positive voltage. Thus the effect of the anode on the adjacent tissue will not be a problem during long term therapy with voltage application, in an analogous manner to the application of low frequency voltage.

A number of electrodes can also be controlled at the same time to provide a multi-phase effect, for example. In this case the oscillator 8 will be formed of several separate oscillators for example, which can be individually controllable with regard to phase, and preferably also with regard to frequency and amplitude, from the control circuit 3. The oscillator 8 can also be controlled to provide a varying output signal with the same sign, either in the form of half period or as amplitudes varied about a direct voltage.

The very slow increase in voltage when determining the suitable voltage can be achieved, for example, by controlling the oscillator 8 to a very low frequency. It is also possible for this purpose to have an extra connectable ramp circuit with a long rise period and with a gentle transition to a sloping decline period.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for applying electrical signals to a heart comprising:

means for generating a voltage signal, during an activation interval, having amplitude changes with each amplitude change having a first derivative associated therewith having an absolute value which is less than an absolute value of a first derivative of an electrical signal which would cause a triggering of a heartbeat in a patient to whom said voltage signal is delivered, said voltage signal having a duration of at least 30 milliseconds; and voltage signal delivery means connected to said means for generating a voltage signal and adapted for in vivo interaction with the heart of said patient, for applying said voltage signal over at least a portion of said heart.

2. An apparatus as claimed in claim 1 wherein said means for generating a voltage signal comprises means for generating a voltage signal having a first derivative with an absolute value which is less than 600 V/sec.

3. An apparatus as claimed in claim 1 further comprising:
   detector means for identifying an abnormal state of said heart and for emitting an abnormal state signal; and
   control means, supplied with said abnormal state signal and connected to said means for generating a voltage, for activating said means for generating a voltage signal for at least one activation interval after receipt of said abnormal state signal by said control means.

4. An apparatus as claimed in claim 1 wherein said means for generating a voltage signal comprises an oscillator which emits a low-frequency alternating voltage, as said voltage signal, having a frequency which is less than 16 Hz, with each half-period of said alternating voltage comprising said activation interval.

5. An apparatus as claimed in claim 1 wherein said means for generating a voltage signal comprises means for generating a voltage signal having a period, an amplitude and a phase associated therewith, and said apparatus further comprising:
   detector means for identifying a current condition of said heart and for generating a detector signal identifying said current condition; and
   control means, supplied with said detector signal and connected to said means for generating a voltage signal, for altering at least one of said period, amplitude or phase dependent on said detector signal.

6. An apparatus as claimed in claim 1 wherein said means for generating a voltage signal comprises means for generating a voltage signal having a period, an amplitude and a phase, and said apparatus further comprising:
   manually operable means in communication with said means for generating a voltage signal for selectively altering at least one of said period, amplitude or phase.

7. An apparatus as claimed in claim 1 further comprising:
   means for generating electrical pacing therapy; and
   pacing electrode means adapted for interaction with said heart for delivering said pacing therapy to said heart superimposed on said heart with said voltage signal.

8. An apparatus as claimed in claim 7 wherein said pacing electrode means comprise said voltage signal delivery means.

9. An apparatus as claimed in claim 1 further comprising:
   means for generating electrical defibrillation therapy; and
   defibrillation electrode means adapted for interaction with said heart for delivering said defibrillation therapy to said heart superimposed on said heart with said voltage signal.

10. An apparatus as claimed in claim 9 wherein said defibrillation electrode means comprise said voltage signal delivery means.

11. An apparatus as claimed in claim 1 wherein said means for generating a voltage signal comprises means for generating a sinusoidal voltage signal.

12. An apparatus as claimed in claim 1 wherein said means for generating a voltage signal comprises means for generating a trapezoidal voltage signal.

13. An apparatus as claimed in claim 1 wherein said means for generating a voltage signal comprises means for generating a triangular voltage signal.

14. An apparatus as claimed in claim 1 wherein said voltage signal has an amplitude, and said apparatus further comprising:
   means for controlling said amplitude of said voltage signal during said activation interval between 0 and 10 V.

15. An apparatus as claimed in claim 1 wherein said voltage signal delivery means comprise a plurality of electrodes, plus a reference electrode adapted for placement outside said heart, with at least one of said plurality of electrodes being selected from the group consisting of an electrode adapted for placement exterior of said heart over a ventricle of said heart, an electrode adapted for placement in the right atrium of said heart, and an electrode adapted for placement in the right ventricle of said heart; and switching means, connected to each of said electrodes of said means for delivering a voltage signal, for selectively connecting said at least one of said plurality of electrodes to said means for generating a voltage signal during said activation interval.

16. An apparatus as claimed in claim 15 wherein said switching means comprises means for simultaneously connecting at least two of plurality of said electrodes to said means for generating a voltage signal during said activation interval.

17. An apparatus as claimed in claim 15 comprising means for generating a plurality of different cardiac therapies, including said means for generating a voltage signal as one of said plurality of therapies, each of said therapies having a different voltage associated therewith;
   said plurality of electrodes comprising respective pairs of electrodes associated with each of said different cardiac therapies;
   control means for selecting at least one of said cardiac therapies for delivery to said heart; and
   said switching means comprising means for connecting the pair of electrodes associated with the selected cardiac therapy to said means for generating different cardiac therapies.

18. An apparatus as claimed in claim 1 wherein said voltage signal delivery means comprise means adapted for delivering said voltage signal from a location originating at an exterior of said patient to said heart of said patient.

19. A method for applying electrical signals to a heart comprising the steps of:
   generating a voltage signal having amplitude changes with each amplitude change having a first derivative associated therewith having an absolute value which is less than an absolute value of a first derivative of an electrical signal for a patient which would cause a triggering of a heartbeat in a patient; and
   applying said voltage in vivo signal over at least a portion of said heart for an application interval of at least 30 milliseconds.

20. A method as claimed in claim 19 wherein the step of generating a voltage signal comprises generating a voltage signal having a first derivative with an absolute value which is less than 600 V/sec.

21. A method as claimed in claim 19 comprising the additional steps of:
   identifying an abnormal state of said heart and emitting an abnormal state signal; and
   applying said voltage signal for at least one activation interval after emission of said abnormal state signal.

22. A method as claimed in claim 19 wherein the step of generating a voltage signal comprises emitting a low-frequency alternating voltage, as said voltage signal, having a frequency which is less than 16 Hz, with each half-period of said alternating voltage comprising said activation interval.

23. A method as claimed in claim 19 wherein the step of generating a voltage signal comprises generating a voltage signal having a period, an amplitude and a phase associated therewith, and said method comprising the additional steps of:

identifying a current condition of said heart and emitting a condition signal identifying said current condition; and altering at least one of said period, amplitude or phase dependent on said condition signal.

24. A method as claimed in claim 19 wherein the step of generating a voltage signal comprises generating a voltage signal having a period, an amplitude and a phase, and said method comprising the additional step of:

manually selectively altering at least one of said period, amplitude or phase.

25. A method as claimed in claim 19 comprising the additional steps of:

generating electrical pacing therapy; and delivering said pacing therapy to said heart superimposed on said heart with said voltage signal.

26. A method as claimed in claim 19 comprising the additional steps of:

generating electrical defibrillation therapy; and delivering said defibrillation therapy to said heart superimposed on said heart with said voltage signal.

27. A method as claimed in claim 19 wherein the step of generating a voltage signal comprises generating a sinusoidal voltage signal.

28. A method as claimed in claim 19 wherein the step of generating a voltage signal comprises generating a trapezoidal voltage signal.

29. A method as claimed in claim 19 wherein the step of generating a voltage signal comprises generating a triangular voltage signal.

30. A method as claimed in claim 19 wherein said voltage signal has an amplitude, and said method comprising the additional step of:

controlling said amplitude of said voltage signal during said activation interval between 0 and 10 V.

31. A method as claimed in claim 19 wherein the step of applying said voltage signal to a heart comprises applying said voltage signal to said heart via a plurality of electrodes, including a reference electrode, adapted for placement outside said heart, and at least one electrode selected from the group consisting of an electrode adapted for placement exterior of said heart over a ventricle of said heart, an electrode adapted for placement in the right atrium of said heart, and an electrode adapted for placement in the right ventricle of said heart; and selectively applying said voltage signal to said heart via said at least one of said plurality of electrodes and said reference electrode during said activation interval.

32. A method as claimed in claim 31 wherein the step of selectively applying said voltage signal comprises simultaneously applying said voltage signal across each of at least two of said plurality of electrodes and said reference electrode during said activation interval.

33. A method as claimed in claim 31 comprising:

generating a plurality of different cardiac therapies, including generating said voltage signal as one of said plurality of therapies, each of said therapies having a different voltage associated therewith;

respectively associating pairs of said plurality of electrodes with each of said different cardiac therapies;

selecting at least one of said cardiac therapies for delivery to said heart; and delivering the selected cardiac therapy in vivo to said heart via the pair of electrodes associated with the selected cardiac therapy.

34. A method as claimed in claim 19 wherein the step of delivering a voltage signal comprises:

originating said voltage signal at an exterior of said patient; and delivering said voltage signal in vivo to said heart from a location at an exterior of said patient.

\* \* \* \* \*